US006572869B2

(12) United States Patent
Douin et al.

(10) Patent No.: US 6,572,869 B2
(45) Date of Patent: *Jun. 3, 2003

(54) COSMETIC COMPOSITIONS COMPRISING AT LEAST ONE CATONIC POLYMER AND AT LEAST ONE NONIONIC ASSOCIATIVE POLYMER

(75) Inventors: Véronique Douin, Paris (FR); Juan Lopez, Paris (FR); Fréderic Cervantes, Paris (FR)

(73) Assignee: L'Oreal S.A., Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/402,781
(22) PCT Filed: Dec. 23, 1998
(86) PCT No.: PCT/FR98/02864
§ 371 (c)(1), (2), (4) Date: Jan. 14, 2000
(87) PCT Pub. No.: WO99/40891
PCT Pub. Date: Aug. 19, 1999

(65) Prior Publication Data
US 2002/0031484 A1 Mar. 14, 2002

(30) Foreign Application Priority Data
Feb. 13, 1998 (FR) .............................. 98/01775

(51) Int. Cl.⁷ ................................. A61K 7/00
(52) U.S. Cl. .................. 424/401; 424/70.1; 514/880; 514/881
(58) Field of Search ............... 424/70.1, 401; 514/880–881

(56) References Cited

U.S. PATENT DOCUMENTS

| 4,833,225 A | 5/1989 | Schaefer et al. .............. 528/28 |
| 4,891,166 A | 1/1990 | Schaefer et al. ......... 260/404.5 |
| 5,294,692 A | 3/1994 | Barron et al. ................ 526/301 |
| 5,344,643 A | 9/1994 | Thiel et al. .................... 424/70 |
| 5,478,562 A * | 12/1995 | Cauwet et al. ............... 424/401 |
| 5,538,717 A | 7/1996 | La Poterie ................... 424/61 |
| 5,661,118 A | 8/1997 | Cauwet et al. ............... 510/126 |

FOREIGN PATENT DOCUMENTS

| DE | 37 05 121 | 9/1988 |
| DE | 37 19 086 | 10/1988 |
| DE | 44 38 846 | 5/1996 |
| EP | 0 282 720 | 9/1988 |
| EP | 0 339 712 | 11/1989 |
| EP | 0 412 705 | 2/1991 |
| EP | 0 415 705 | 3/1991 |
| EP | 0 530 974 | 3/1993 |
| EP | 0 555 155 | 8/1993 |
| EP | 0 617 607 | 10/1994 |
| EP | 0 637 600 | 2/1995 |
| EP | 0 648 485 | 4/1995 |
| EP | 0 714 654 | 6/1996 |
| EP | 0 745 373 | 12/1996 |
| EP | 0 824 914 | 2/1998 |
| FR | 2 733 910 | 11/1996 |
| FR | 2 738 835 | 3/1997 |
| FR | 2 750 047 | 12/1997 |
| FR | 2 758 262 | 7/1998 |
| WO | WO 96/37591 | * 11/1996 |

OTHER PUBLICATIONS

Zeying Ma et al., "Phase Behaviors and Film Properties of Dispersions and Coatings Containing Associative and Conventional Thickeners", Journal of Applied Polymer Science, vol. 49, 1993, ¶. 1509–1527.
English language Derwent Abstract of DE 37 05 121.
English language Derwent Abstract of DE 44 38 846.
English language Derwent Abstract of EP 0 637 600.
English language Derwent Abstract of EP 0 714 654.
English language Derwent Abstract of EP 0 745 373.
English language Derwent Abstract of FR 2 738 835.
English language Derwent Abstract of FR 2 733 910.
English language Derwent Abstract of FR 2 750 047.
English language Derwent Abstract of FR 2 758 262.

* cited by examiner

Primary Examiner—Jose G. Dees
Assistant Examiner—Konata M. George
(74) Attorney, Agent, or Firm—Finnegan, Henderson, Farabow, Garrett & Dunner, LLP

(57) ABSTRACT

A cosmetic composition comprising, in a cosmetically acceptable medium, at least one cationic polymer containing at least one acrylamide unit or acrylamide derivative, and at least one nonionic associative polymer containing at least one fatty chain.

20 Claims, No Drawings

COSMETIC COMPOSITIONS COMPRISING AT LEAST ONE CATONIC POLYMER AND AT LEAST ONE NONIONIC ASSOCIATIVE POLYMER

The present invention relates to cosmetic hair compositions comprising a combination of at least one cationic polymer and at least one nonionic associative polymer, as well as to their use as conditioners in particular.

The importance of cationic polymers as cosmetic components for treating and protecting the hair has been known for a long time. By virtue of their considerable substantivity for the hair, they improve the hair's cosmetic properties. However, in the field of hair care, cationic polymers have never been able to advantageously replace cationic surfactants of quaternary ammonium type, which give better quality performance in cosmetic terms but most of them have a certain number of problems such as less than perfect eye tolerance and appreciable environmental toxicity.

Moreover, surfactants of quaternary ammonium type in combination with fatty alcohols are conventionally used to thicken conditioners. However, these thick emulsions have the cumulative drawbacks of their constituents, namely the problems described above due to the presence of cationic surfactants and an effect of making the hair feel lank by depositing fatty alcohols.

The use of conventional thickeners, i.e. water-soluble polymers, has hitherto not made it possible to obtain satisfactory rheological properties. These formulations are often too runny and sticky when the desired level of viscosity is reached.

One very advantageous recent approach consisted in using, as thickeners, polymers capable of associating reversibly with each other or with other molecules. Such polymers are known as "associative polymers". One specific case of associative polymers is amphiphilic polymers, i.e. polymers comprising one or more hydrophilic portions which make them soluble in water, and one or more hydrophobic regions via which the polymers interact and assemble with each other or with other components.

It is known practice to prepare hair compositions in the form of a gel using, as a thickening system, such associative amphiphilic polymers, in conjunction with surfactants. It is thought that the advantageous rheological properties of the gels thus obtained result from the formation of mixed micelles formed from the surfactants and the hydrophobic portions of the amphiphilic polymers, these micelles constituting a multitude of physical crosslinking points.

European patent application EP-A-0,415,705 describes a thickening system for rinse-out conditioners consisting of a first thickener which is a water-soluble polymer modified with $C_8$–$C_{22}$ hydrophobic groups, and a secondary thickener which is a water-soluble polymer with a molar mass of greater than about 20,000.

The Applicant has now discovered that the combination of a certain type of cationic polymer which has advantageous cosmetic properties with a nonionic associative polymer makes it possible not only to obtain thickened formulations which have a very pleasant texture, but also to improve the cosmetic performance quality of the cationic polymer.

A subject of the present invention is consequently a cosmetic composition comprising, in a cosmetically acceptable medium, at least one cationic polymer containing at least one acrylamide unit or acrylamide derivative and at least one nonionic associative polymer containing at least one fatty chain.

Another subject of the present invention is the use of a cationic polymer containing at least one acrylamide unit or acrylamide derivative in combination with at least one nonionic associative polymer containing at least one fatty chain, for thickening a cosmetically acceptable medium.

A third subject of the invention is a cosmetic process for treating the hair with the cosmetic compositions thickened by the combination of a cationic polymer containing at least one acrylamide unit or acrylamide derivative and at least one nonionic associative polymer containing at least one fatty chain.

Other subjects will become apparent on reading the description and the examples which follow.

The cosmetic compositions in accordance with the invention are essentially characterized in that they contain, in a cosmetically acceptable support, (A) at least one cationic polymer containing at least one acrylamide unit or acrylamide derivative, and (B) at least one nonionic associative polymer containing at least one fatty chain.

The cationic polymers used as component (A) in the compositions of the invention are preferably polymers comprising at least one unit of type I and at least one unit of type II or II' or III or III' corresponding to the formulae below:

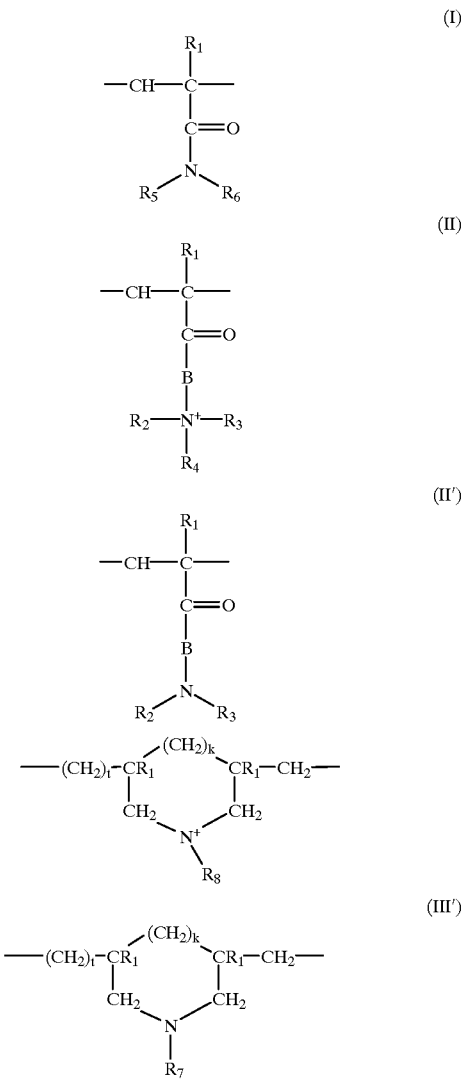

in which

R$_1$ represents a hydrogen atom or a methyl group,

B represents a group A or a group NH-A,

A represents a C$_1$–C$_6$ alkylene group,

R$_2$, R$_3$ and R$_4$ represent, independently of each other, a C$_1$–C$_6$ alkyl group, R$_5$ and R$_6$ represent, independently of each other, a hydrogen atom or a C$_1$–C$_6$ alkyl group, R$_7$ and R$_8$, independently of each other, denote an alkyl group containing from 1 to 22 carbon atoms, a hydroxyalkyl group in which the alkyl group preferably contains from 1 to 5 carbon atoms, or a lower amidoalkyl group (1 to 5 carbon atoms), or R$_7$ and R$_8$ can denote, together with the nitrogen atom to which they are attached, a heterocyclic group such as piperidyl or morpholinyl, k and t are equal to 0 or 1, the sum (k+t) being equal to 1, and X$^-$ represents an organic or inorganic anion.

According to the invention, the expression "lower C$_1$–C$_6$ alkyl group" means an alkyl group containing a linear or branched chain comprising from 1 to 6 carbon atoms, such as methyl, ethyl, n-propyl, n-butyl, n-pentyl and n-hexyl radicals, as well as the corresponding branched isomers.

According to the invention, the expression "C$_1$–C$_6$ alkylene group" means a group chosen from methylene, ethylene, 1,3-propylene, 1,4-butylene, 1,5-pentylene and 1,6-hexylene groups, or the branched isomers thereof.

In one preferred embodiment of the invention, a cationic copolymer is used comprising at least one unit of type I and one unit of type II.

In an even more particularly preferred embodiment of the invention, a cationic copolymer is used comprising at least one unit of type I and one unit of type II above in which R$_1$ represents a methyl group, B represents an ethylene group, R$_2$, R$_3$ and R$_4$ each represent a methyl group, R$_5$ and R$_6$ each represent a hydrogen atom and X$^-$ is a chloride ion.

A poly(dimethyldiallylammonium chloride/acrylamide) copolymer sold under the name Merquat® 550 by the company Calgon can be used as cationic polymer of the invention.

Preferred examples of cationic polymers used as component (A) are a crosslinked copolymer of trimethylammonioethyl methacrylate chloride and acrylamide sold by the company Allied Colloids under the name Salcare® SC 92, a non-crosslinked copolymer of trimethylammonioethyl methacrylate chloride and acrylamide, sold under the name Bina Quat® P100 by the company Ciba Geigy, under the name Polytec® 95 by the company Polytec, and under the name Nalquat® by the company Nalco, and a non-crosslinked copolymer of trimethylammonioethyl methacrylate chloride and methacrylamide, sold under the name Rohagit KF® 720F by the company Rohm. Even more preferably, the polymer Salcare® SC 92 will be used.

In accordance with the invention, the expression "associative polymers" means amphiphilic polymers comprising hydrophilic portions and hydrophobic regions which, in aqueous medium, will have a tendency to assemble with each other or with other molecules. These hydrophobic portions can be, for example, side fatty chains or terminal fatty chains introduced by copolymerization or by grafting, or alternatively they form part of the main chain of the polymer.

The nonionic amphiphilic polymers according to the present invention, which are used as component (B), are preferably chosen from:

(1) celluloses modified with groups comprising at least one C$_8$–C$_{22}$ fatty chain, for example hydroxyethylcellulose modified with groups comprising at least one C$_8$–C$_{22}$ fatty chain. Such a product is, for example, Natrosol Plus Grade 330 (C$_{16}$ alkyl chains), sold by the company Aqualon, or alternatively Bermocoll EHM 100 sold by the company Berol Nobel; or celluloses modified with alkylphenyl polyalkylene glycol ether groups, such as the product Amercell Polymer® HM-1500 sold by the company Amerchol;

(2) hydroxypropyl guars modified with groups comprising at least one C$_8$–C$_{22}$ fatty chain, such as the product Esaflor® HM 22 sold by the company Lamberti, and the products Miracare® XC95-3 and RE205-1 sold by the company Rhône Poulenc;

(3) polyurethanes comprising at least one C$_8$–C$_{22}$ fatty chain, such as the products Dapral®T210 and Dapral®T212, sold by the company Akzo, or the products Acrysol®46 and DW 1206 F sold by the company Rohm & Haas;

(4) copolymers of vinylpyrrolidone and hydrophobic monomers containing a C$_8$–C$_{22}$ fatty chain, such as, for example, the products Antaron® V216, Antaron® V220, Ganex® V261 and Ganex® V220 sold by the company ISP;

(5) copolymers of C$_1$–C$_6$ alkyl methacrylates or acrylates and amphiphilic monomers comprising at least one C$_8$–C$_{22}$ fatty chain, such as, for example, the oxyethylenated methyl methacrylate/stearyl acrylate copolymer sold by the company Goldschmidt under the name Antil® 208;

(6) copolymers of hydrophilic methacrylates or acrylates and hydrophobic monomers comprising at least one C$_8$–C$_{22}$ fatty chain, such as, for example, the copolymer of polyethylene glycol methacrylate/lauryl methacrylate.

(7) fatty-chain starches, (8) fatty-chain proteins.

The cationic polymers and the nonionic associative polymers of the present invention are used in the compositions of the invention in amounts which are sufficient to obtain a satisfactory thickening of the aqueous medium, thus allowing the composition to be applied and distributed uniformly on the hair. Such a composition has a viscosity of between 100 centipoises (cP) and 100 poises (P), preferably between 200 centipoises (cP) and 50 poises (P).

An amount of cationic polymer of between 0.05 and 10% by weight, preferably between 0.1 and 5% by weight, of active material relative to the total weight of the composition is used in particular.

The nonionic associative polymers used in the present invention are present in a proportion of from 0.05 to 10% by weight, preferably in a proportion of from 0.1 to 5% by weight, of active material relative to the total weight of these composition.

The cosmetically acceptable medium preferably consists of water and can also contain cosmetically acceptable solvents, for example lower monoalcohols such as ethanol or isopropanol, glycols such as diethylene glycol, glycol ethers such as ethylene glycol alkyl ether or diethylene glycol alkyl ether, or alternatively fatty acid esters, these solvents being used alone or in the form of a mixture.

The cosmetic hair compositions of the present invention can also contain one or more commonly used additives. Examples which may be mentioned are fatty alcohols, fatty acid esters of fatty alcohols, fragrances, dyes, preserving agents, sunscreens, proteins, alkylated proteins, quaternized proteins, vitamins and provitamins, pH regulators, anionic, cationic, nonionic or amphoteric surfactants, silicones, volatile silicones, silicone oils, silicone gums, amino silicones, quaternized silicones, alkylated silicones, grafted silicones, silicone emulsions, mineral and plant oils, plant waxes, ceramides or pseudoceramides and polymers other than those according to the invention defined above. It is clearly understood that the choice of these compounds must take into account any interactions with the thickening system. A person skilled in the art will take care to ensure that the addition of these additives does not have an adverse effect on the advantageous properties of the compositions obtained according to the present invention.

One cosmetic process for treating the hair according to the invention consists in applying a cosmetic composition defined above to the hair, in distributing it homogeneously and, after leaving it on the hair for a suitable period, in optionally rinsing and then drying the hair thus treated.

The examples which follow are intended to illustrate the invention without thereby being limiting in nature.

EXAMPLES

Table 1 shows cosmetic compositions obtained by combining, in water, various cationic polymers (component (A)) and an associative polymer of the present invention (component (B)).

The cationic polymers shown are copolymers of acrylamide and trimethylammonioethyl methacrylate chloride which is crosslinked (Salcare® SC92 from the company Allied Colloids) or non-crosslinked (Rohagit® KF720 from the company Rohm)).

The comparative polymers are
- a hydroxyethylcellulose crosslinked with epichlorohydrin and bearing trimethylammonium groups (Celquat® SC240 from Union Carbide),
- a quaternized copolymer of vinylpyrrolidone and dimethylaminoethyl methacrylate (Gafquat® 855 from the company GAF), and
- a polycondensate of tetramethylhexamethylenediamine and 1,3-dichloropropylene (polymer C).

It is seen that only the cationic polymers in accordance with the present invention give rise to greater thickening with the associative polymer, their cosmetic effect being improved by this polymer.

Table 2 shows cosmetic compositions combining, in water, a preferred cationic polymer of the invention (component (A)) with different associative polymers in accordance with the invention (component (B)). All these associative polymers in combination with Salcare® SC92 give a satisfactory thickening effect and make it possible to obtain cosmetic compositions which have excellent cosmetic performance qualities.

It can be seen that these advantageous results, both in terms of the cosmetic properties and in terms of the formulation, are obtained in the absence of cationic surfactants.

It is clearly understood that the description hereinabove has been given purely for illustrative purposes and without any implied limitation, and that variants or modifications may be applied thereto in the context of the present invention.

TABLE 1

| Component (A) | Amount of (A) (as a % of active material) | Component (B) | Amount of (B) as a % of active material | Thickening (viscosity in poises (P)) | Cosmetic properties |
|---|---|---|---|---|---|
| Salcare SC92 | 0.5 | Acrysol 46 | 1 | Very good (viscosity: 18 P) | Good cosmetic properties, better than those of (A) alone |
| Rohagit KF720 | 0.95 | Acrysol 46 | 1 | Good (viscosity: 3.5 P) | Good cosmetic properties, better than those of (A) alone |
| Celquat SC240 | 0.5 | Acrysol 46 | 1 | No thickening | Poor cosmetic properties, identical to those of (A) alone |
| Gafquat 855 | 0.5 | Acrysol 46 | 1 | No thickening | Poor cosmetic properties, identical to those of (A) alone |
| Polymer C | 1 | Acrysol 46 | 1 | No thickening | Identical to those of (A) alone |

TABLE 2

| Component (A) | Amount of (A) (as a % of active material) | Component (B) | Amount of (B) as a % of active material | Thickening (viscosity in poises (P)) | Cosmetic properties |
|---|---|---|---|---|---|
| Salcare SC92 | 0.5 | Acrysol 46 | 1 | Very good (viscosity: 18 P) | Good cosmetic properties, better than those of (A) alone |
| Salcare SC92 | 0.5 | Dapral T212 | 1 | Good (viscosity: 4.9 P) | Good cosmetic properties, better than those of (A) alone |
| Salcare SC92 | 0.5 | DW 1206 F | 1 | Very good (viscosity: 40 P) | Good cosmetic properties, better than those of (A) alone |
| Salcare SC92 | 0.5 | Natrosol Plus | 1 | Very good (viscosity: 12 P) | Good cosmetic properties, better than those of (A) alone |

What is claimed is:

1. A cosmetic composition comprising, in a cosmetically acceptable medium, (A) at least one cationic polymer containing at least one acrylamide unit or acrylamide derivative, and (B) at least one nonionic associative polymer containing at least one fatty chain, with the proviso that said at least one cationic polymer is not a dimethyldiallylammonium chloride/acrylamide copolymer in an amount of 0.5 g when said at least one nonionic associative polymer is PPG-14 laureth-60 alkyl dicarbamate in an amount of 2 g.

2. The composition according to claim 1, wherein the at least one cationic polymer is a polymer comprising at least one unit of formula I below and at least one unit chosen from formula II, II', III, and III" below:

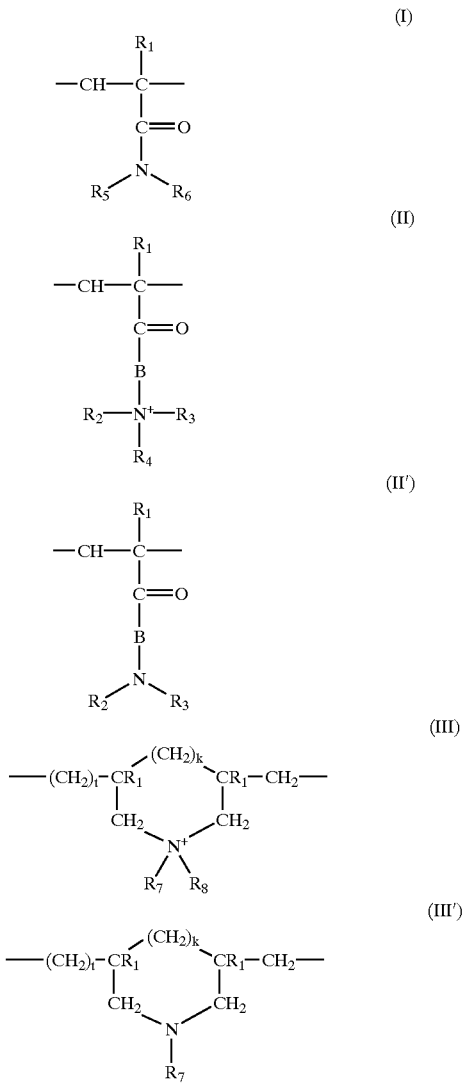

in which
R$_1$ is chosen from hydrogen and methyl groups,
B is chosen from group A and group NH-A,
wherein A is a C$_1$–C$_6$ alkylene group,
R$_2$, R$_3$ and R$_4$ are, independently of each other, C$_1$–C$_6$ alkyl groups,
R$_5$ and R$_6$ are, independently of each other, chosen from hydrogen and C$_1$–C$_6$ alkyl groups,
R$_7$ and R$_8$ are, independently of each other, chosen from alkyl groups containing from 1 to 22 carbons, hydroxyalkyl groups, and lower amidoalkyl groups having 1 to 5 carbons, or
R$_7$ and R$_8$, together with the nitrogen atom to which they are attached, form a heterocyclic group,
k and t are equal to 0 or 1, the sum (k+t) being equal to 1, and
X$^-$ is chosen from organic and inorganic anions.

3. The composition of claim 2, wherein R$_7$ and R$_8$ are, independently of each other, chosen from hydroxyalkyl groups in which the alkyl group contains from 1 to 5 carbons.

4. The composition of claim 2, wherein R$_7$ and R$_8$, together with the nitrogen atom to which they are attached, form a heterocyclic group chosen from piperidyl and morpholinyl.

5. The composition according to claim 2, wherein R$_1$ is a methyl group, B is an ethylene group, R$_2$, R$_3$ and R$_4$ are each a methyl group, R$_5$ and R$_6$ are each a and X$^-$ is a chloride ion.

6. The composition according to claim 1, the at least one cationic polymer containing at least one acrylamide unit or acrylamide derivative is chosen from a crosslinked copolymer of trimethylammonioethyl methacrylate chloride and acrylamide, a noncrosslinked copolymer of trimethylammonioethyl methacrylate chloride and acrylamide, and a noncrosslinked copolymer of trimethylammonioethyl methacrylate chloride and methacrylamide.

7. The composition according to claim 1, wherein the at least one nonionic associative polymer containing at least one fatty chain is chosen from:
 (1) celluloses modified with groups comprising at least one C$_8$–C$_{22}$ fatty chain;
 (2) hydroxypropyl guars modified with groups comprising at least one C$_8$–C$_{22}$ fatty chain;
 (3) polyurethanes comprising at least one C$_8$–C$_{22}$ fatty chain;
 (4) copolymers of vinylpyrrolidone and hydrophobic monomers containing a C$_8$–C$_{22}$ fatty chain;
 (5) copolymers of C$_1$–C$_6$ alkyl methacrylates or acrylates and amphiphilic monomers comprising at least one fatty chain;
 (6) copolymers of hydrophilic methacrylates or acrylates and hydrophobic monomers comprising at least one C$_3$–C$_{22}$ fatty chain;
 (7) fatty-chain starches; and
 (8) fatty-chain proteins.

8. The composition according to claim 7, wherein the at least one nonionic associative polymer containing at least one fatty chain is chosen from PEG-150/stealyl alcohol/Saturated methylene diphenyldiisocyanate copolymer, PPG-14 palmeth 60 alkyl dicarbamate, DW 1206 F, and cetyl hydroxyethylcellulose.

9. The composition according to claim 1, wherein the at least one cationic polymer containing at least one acrylamide unit or acrylamide derivative is present in a amount of from 0.05 to 10% by weight of active material relative to the total weight of the composition.

10. The composition according to claim 9, wherein the at least one cationic polymer containing at least one acrylamide unit or acrylamide derivative is present in a amount of from 0.1 to 5% weight of active material relative to the total weight of the composition.

11. The composition according to claim 1, wherein the at least one nonionic associative polymer containing at least one fatty chain is present in an amount of from 0.05 to 10% by weight of active material relative to the total weight of the composition.

12. The composition according to claim 11, wherein at least one nonionic associative polymer containing at least one fatty chain is present in an amount of from 0.1 to 5% by weight of active material relative to the total weight of the composition.

13. The composition according to claim 1, wherein the cosmetically acceptable medium is water.

14. The composition according to claim 13, wherein the cosmetically acceptable medium further comprises cosmetically acceptable solvents chosen from lower monoalcohols, glycols, glycol ethers, or fatty acid esters, and mixtures thereof.

15. The composition according to claim 14, wherein said monoalcohols are chosen from ethanol and isopropanol, wherein said glycols is a diethylene glycol, and wherein said glycol ethers are chosen from ethylene glycol alkyl ethers and diethylene glycol alkyl ethers.

16. The composition according to claim 1, further comprising one or more additives chosen from fatty alcohols, fatty acid esters of fatty alcohols, fragrances, dyes, preserving agents, sunscreens, proteins, alkylated proteins, quaternized proteins, vitamins and provitamins, pH regulators, anionic, cationic, nonionic and amphoteric surfactants, silicones, volatile silicones, silicone oils, silicone gums, amino silicones, quaternized silicones, alkylated silicones, grafted silicones, silicone emulsions, mineral and plant oils, plant waxes, ceramides, pseudoceramides and other polymers that are different from said component (A) and said component (B).

17. A hair conditioner comprising, in a cosmetically acceptable medium:

(A) at least one cationic polymer containing at least one acrylamide unit or acrylamide derivative, and (B) at least one nonionic associative polymer containing at least one fatty chain, with the proviso that said at least one cationic polymer is not a dimethyldiallylammonium chloride/acrylamide copolymer in an amount of 0.5 g when said at least one nonionic associative polymer is PPG-14 laureth-60 alkyl dicarbamate in an amount of 2 g.

18. A process of thickening a cosmetic composition comprising adding at least one cationic polymer comprising at least one acrylamide unit or acrylamide derivative and at least one nonionic associative polymer containing at least one fatty chain to the composition in an amount effective to thicken said composition.

19. A process for treating hair comprising applying to the hair a composition comprising, in a cosmetically acceptable medium:

(A) at least one cationic polymer containing at least one acrylamide unit or acrylamide derivative, and (B) at least one nonionic associative polymer containing at least one fatty chain, with the proviso that said at least one cationic polymer is not a dimethyldiallylammonium chloride/acrylamide copolymer in an amount of 0.5 g when said at least one nonionic associative polymer is PPG-14 laureth-60 alkyl dicarbamate in an amount of 2 g.

20. The process of claim 19, wherein prior to drying the treated hair, the hair is rinsed.

* * * * *

UNITED STATES PATENT AND TRADEMARK OFFICE
CERTIFICATE OF CORRECTION

PATENT NO. : 6,572,869 B2
DATED : June 3, 2003
INVENTOR(S) : Véronique Douin et al.

It is certified that error appears in the above-identified patent and that said Letters Patent is hereby corrected as shown below:

<u>Title page, Item [54] and Column 1, line 2,</u>
"CATONIC" should read -- CATIONIC --.

<u>Column 7,</u>
Line 4, "III'"" should read -- III' --.

<u>Column 8,</u>
Line 7, "a and" should read -- a hydrogen atom, and --.
Line 9, "claim 1, the" should read -- claim 1, wherein the --.
Line 32, "$C_3$-$C_{22}$" should read -- $C_8$-$C_{22}$ --.
Line 37, "PEG-150/stealyl" should read -- PEG-150/stearyl --.
Line 38, "Saturated methylene diphenyldilsocyanate" should read
-- saturated methylene diphenyldiisocyanate --.
Lines 43 and 48, "a amount" should read -- an amount --.
Line 49, "5% weight" should read -- 5% by weight --.

<u>Column 9,</u>
Line 3, "glycols is a diethylene glycol," should read -- glycols are diethylene glycols, --.

Signed and Sealed this

Sixth Day of January, 2004

JAMES E. ROGAN
*Director of the United States Patent and Trademark Office*